United States Patent
Keller

(10) Patent No.: US 6,224,634 B1
(45) Date of Patent: May 1, 2001

(54) HIP-JOINT ENDOPROSTHESIS

(75) Inventor: Arnold Keller, Kayhude (DE)

(73) Assignee: Waldemar Link (GmbH & Co.), Hamburg (DE)

( * ) Notice: Subject to any disclaimer, the term of this patent is extended or adjusted under 35 U.S.C. 154(b) by 0 days.

(21) Appl. No.: 09/381,751

(22) PCT Filed: Mar. 2, 1998

(86) PCT No.: PCT/EP98/01158

§ 371 Date: Sep. 23, 1999

§ 102(e) Date: Sep. 23, 1999

(87) PCT Pub. No.: WO98/42279

PCT Pub. Date: Oct. 1, 1998

(30) Foreign Application Priority Data

Mar. 26, 1997 (DE) .......................................... 297 05 500 U

(51) Int. Cl.[7] ...................................................... A61F 2/36
(52) U.S. Cl. ..................................... 623/23.11; 623/23.15; 623/23.36
(58) Field of Search ............................... 623/23.11, 23.14, 623/23.15, 23.31, 23.36, 16.11, 18.11, 20.11, 22.11, 22.15, 22.4

(56) References Cited

U.S. PATENT DOCUMENTS

| | | | |
|---|---|---|---|
| 2,934,065 | * | 4/1960 | Townley .......................... 623/22.11 |
| 4,279,042 | * | 7/1981 | Andriacchi et al. .............. 623/23.11 |
| 4,359,785 | * | 11/1982 | Niederer ........................... 623/23.11 |
| 4,658,808 | * | 4/1987 | Link .................................. 623/16.11 |
| 4,938,771 | * | 7/1990 | Vecsei et al. ..................... 623/23.11 |
| 5,222,985 | * | 6/1993 | Homsy .............................. 623/23.11 |

FOREIGN PATENT DOCUMENTS

| | | |
|---|---|---|
| 0 477 113A1 | 3/1992 | (EP) . |
| 0 579 868 A2 | 1/1994 | (EP) . |
| 0 666 069 A1 | 8/1995 | (EP) . |
| 0 711 534 A1 | 5/1996 | (EP) . |
| 2 429010 | 1/1980 | (FR) . |
| 2 629 707 | 10/1989 | (FR) . |
| 2 636 837 | 3/1990 | (FR) . |
| 2 706 283 | 12/1994 | (FR) . |
| 2 069 340 | 8/1981 | (GB) . |

* cited by examiner

*Primary Examiner*—Pedro Philogene
(74) *Attorney, Agent, or Firm*—Morrison & Foerster LLP

(57) ABSTRACT

A hip-joint endoprosthesis with a stem to be anchored in the femur, and with a joint head supported by the stem via a neck. In order, upon implantation, to be able to use one and the same prosthesis with a different choice of resection plane within the neck of the head, the stem of the prosthesis is curved in a substantially uniform circular arc; the neck adjoins the upper end of the stem approximately in the same direction; the length of the stem is not greater than 150 mm; and the hip-joint endoprosthesis, while keeping the same stem shape, is available with different neck lengths, of which several are smaller than the length of an average natural femoral neck.

16 Claims, 2 Drawing Sheets

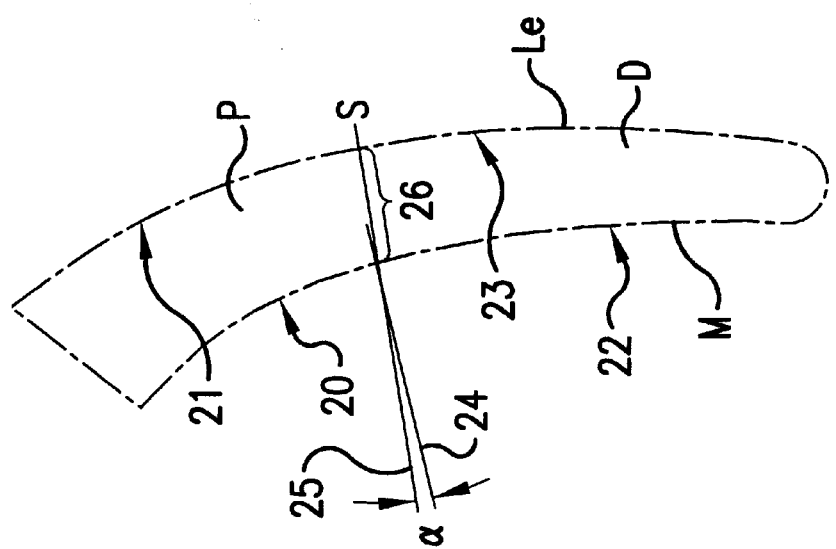
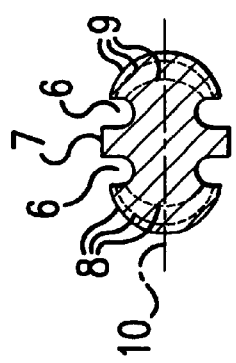
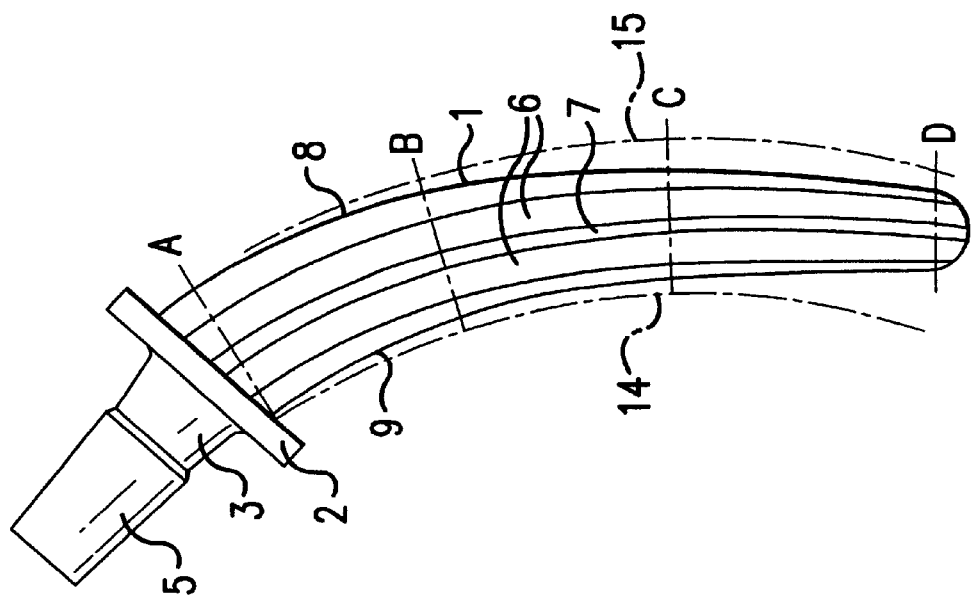

HIP-JOINT ENDOPROSTHESIS

BACKGROUND OF THE INVENTION

In the early years of prosthetic surgery of the hip-joint, attempts were made to replace only the joint head with an implant held by a straight stem, which was held by the femoral neck and the spongy substance of the adjoining epiphysis of the femur. It was found that this arrangement was inadequate for transmitting the forces to the femur. Hip prostheses are therfore mostly used whose stem reaches into the diaphysis of the bone (FR-A-2,636,837, U.S. Pat. No. 5,413,610, GB-A-2,069,340; EP-A-477,113, FR-A-2,706, 283, EP-A-711,534, FR-A-2,629,707, FR-A-2,429,010). To obtain sufficient access for this, the femoral neck is completely resected. In recent years, hip prostheses have been proposed which allow the femoral neck to be preserved. The resection is carried out immediately below the joint head (EP-A-666,069, col. 2, l. 47; EP-A-579,868, col. 8, l. 51; WO 87/00033, p. 6, col. 19). A collar-like neck bearing is provided which is supported on the resection surface of the femoral neck. The distance of the support surface of the neck bearing from the center of the joint head of the prosthesis is unchangeable because variations are ruled out as a result of the resection immediately below the joint head. By contrast, in the case of conventionally implanted hip prostheses, it is known (FR-A-2,429,010, FR-A-2,629,707, U.S. Pat. No. 5,413,610, FR-A-2,636,837) to keep-in stock different neck lengths of the prosthesis for the purpose of compensating for different neck lengths of the bone that is to be replaced.

SUMMARY OF THE INVENTION

The invention starts from that type of prosthesis which seeks to preserve the natural femoral neck (EP-A-666 069). The object of the invention is to achieve greater versatility of use, which, if appropriate, can be decided upon even during the operation.

The solution according to the invention lies in the features disclosed herein. In a hip-joint endoprosthesis (hereinafter hip-joint prosthesis) with a stem which is to be anchored in the femur, is curved substantially uniformly in a circular arc and has a length of not more than 150 mm, and with a neck which adjoins the upper end of the stem approximately in the same direction and whose length is smaller than the length of an average natural femoral neck and supports a joint head, a stem shape is provided whose geometric conditions in the projection on the LM plane (lateral-medial plane) are:

- the medial contour in the proximal section follows a circular arc with radius K·7,2 and in the distal section follows a contiguous circular arc with radius K·27;
- the lateral contour in the proximal section follows a circular arc with radius K·12,4 and in the distal section follows a contiguous circular arc with radius K·21;
- the circular arcs determining the two contours have, at the crossover point from the proximal to the distal section, which is the same for the lateral and medial contour, a distance of 1.9 cm;
- the radii of the lateral and medial circular arcs form an angle of 3.8° to one another at the crossover point;
- K is a constant of between 0.8 and 1.1 cm uniform for each prosthesis;
- the deviations of the actual contours from the said circular arcs are not greater than 3 mm.

The contours of different prosthesis sizes are linked to one another by the scaling factor K.

This combination of features allows the physician, depending on the conditions he finds during the operation, to preserve the femoral neck in its entirety, partially, or not at all. Depending on the circumstances of the case, he implants the prosthesis according to the invention at a greater or lesser depth and is thus able to find the best possible compromise between preserving as much bone material as possible, on the one hand, and creating a stable prosthetic support, on the other hand. Especially in the case of younger patients, it is important, during the first prosthesis implantation, to preserve as much bone substance as possible with a view to an anticipated second prosthesis fitting or even a third prosthesis fitting.

By virtue of the said features, it is possible, depending on the position of the resection plane, for the stem to be inserted parallel to itself on a correspondingly curved path through the femoral neck into the adjoining part of the femur.

Although the tip of the stem can project as far as the diaphysis, according to the invention this is possible only over a limited length; nevertheless, the prosthesis stem reaches into that area of the femur which ensures good support by virtue of the thickness of its cortical bone. The stem length is preferably still considerably smaller than 150 mm, namely of the order of 100 to 140 mm, more preferably up to 130 mm.

The length is to be measured from the center of the upper end of the stem (below the neck bearing, if present) in a straight line as far as the tip of the stem. The depth at which the prosthesis sits in the bone thus depends on the degree of resection of the femoral neck. To ensure that the joint head nevertheless sits at the desired location, independently of the degree of resection of the femoral neck, different neck lengths are provided according to the invention. The available neck lengths are for that reason shorter than the average natural femoral neck length, since in general at least part of the femoral neck length is left in place.

While the known prostheses all require a predetermined resection plane, namely either directly below the joint head or at the distal end of the femoral neck, this is not the case with the prosthesis according to the invention. Instead, the uniform curvature of the stem has the effect that it can be implanted at different depths, with the different position of the resection plane in relation to the joint head being compensated for by the choice of a suitable neck length. This is most easily done by equipping the neck with a plug cone for connection to the joint head and by making available joint heads which have different attachment lengths.

It can be expedient for the stem in the projection on the plane including the lateral and medial contours to lie between two concentric circles whose spacing is equal to the greatest thickness of the stem.

In the view from the lateral direction, the contour of the stem follows the course of the bone. It is also particularly expedient to accurately simulate the anteversion of the neck and to provide correspondingly different stem configurations for the two sides of the body.

The stem preferably has a multiplicity of deep grooves exclusively on its front and its rear, the course of the grooves being parallel to the curvature of the stem. These grooves take up bone material and thus contribute to supporting the stem in cases of cementless implantation. By virtue of their course being parallel to the curvature of the stem, they assist, by means of their guiding properties, in the correct introduction of the prosthesis into the bone upon a curved trajectory parallel to themselves.

The lower section of the prosthesis stem, which takes up approximately a third of its overall length, can have a smaller curvature than the remaining upper part of the stem. This curvature can be smaller, the more the thickness of the stem decreases towards its lower end.

BRIEF DESCRIPTION OF THE DRAWINGS

The invention is explained in greater detail below with reference to the drawings in which:

FIG. 4 shows a side view of the prosthesis on an approximately natural scale, FIG. 5 shows stem cross-sections at points A, B and C, FIG. 6 shows the stem cross-section at point D, FIG. 7 shows the geometric conditions for the outline contour of the prosthesis stem in the projection on the plane including the lateral and medial contours.

DETAILED DESCRIPTION OF THE INVENTION

Figure 1:
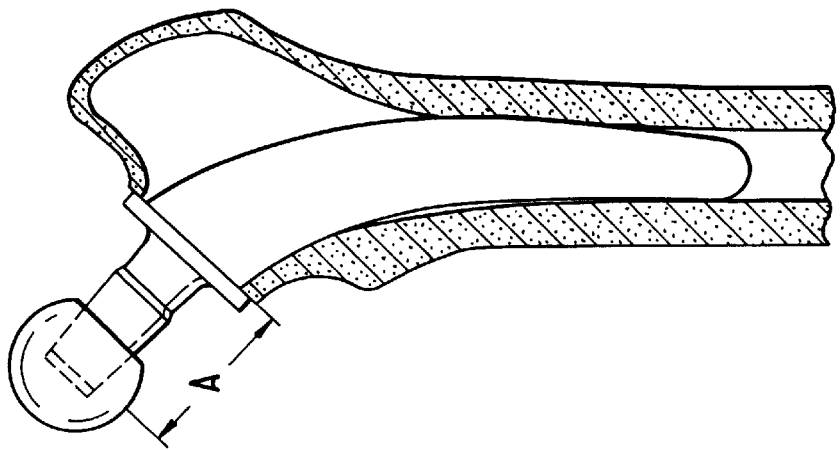
FIGS. 1 to 3 show views of the prosthesis in the projection on the plane including the lateral and medial contours, with different positioning of the resection surface.
Figure 2:
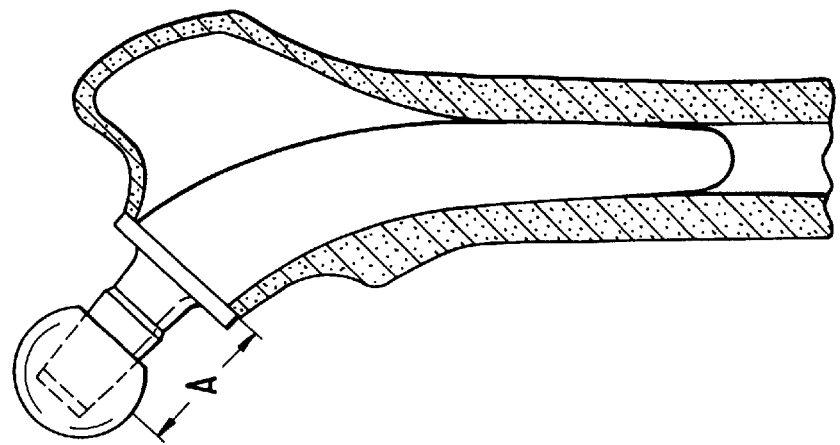
Figure 3:
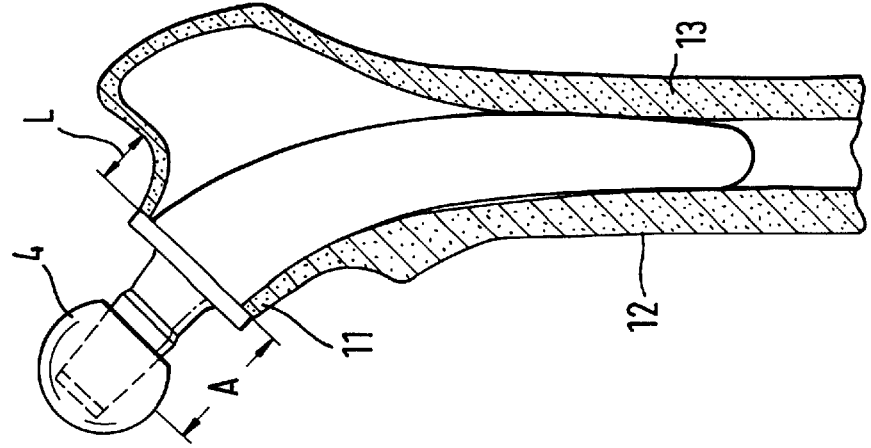

The prosthesis consists of a stem 1, terminating at the top in a neck bearing 2, of a neck 3 and of a head 4, which contains a conical bore for attachment to the cone 5 which terminates the prosthesis at the top. As can be seen from comparing FIGS. 1 to 3, the heads 4 have a different bore diameter, the result of which is that the distance A, which is the distance between the bottom surface of the neck bearing 2 and the center of the head 4, is different.

The stem 1 of the prosthesis is strongly curved in the projection on the plane including the lateral and medial contours, in which it is shown in the drawing. In the example illustrated in FIG. 4, the lateral and medial stem boundary lies between two concentric circular arcs 14 and 15 whose spacing corresponds to the maximum stem thickness. The curvature of its centre line in the upper two thirds (to approximately the cutting plane C) follows a circular arc. The radius of the center line, indicated by dot-and-dash lining, preferably lies between 7 and 15 cm, more preferably between 9 and 13 cm. It is preferably concentric to the circular arcs 14, 15 in the upper two thirds of the stem length. In the lower section on the other side of the cutting line C, the stem is likewise curved, but with a greater radius of curvature. It can also be straight here if it is correspondingly short, that is to say expediently no longer than half the uniformly curved stem length. However, it is preferably also slightly curved and can then also be correspondingly longer in relation to the upper stem section. In the case shown, its length measured along the centre line represents approximately two thirds of the uniformly curved section above the cutting line C.

In cross-section the stem is preferably of elongate shape, with the longer axis in the LM direction. Its extent in the AP direction in the central area is approximately constant in the upper third of the stem length (between the cutting lines A and B) and from there tapers approximately uniformly to the tip. In this way, in the projection on a horizontal plane, it provides in the upper third a comparatively large surface area for the transmission of vertical forces. The cross-sectional development can best be seen from FIG. 5, in which the cross-sectional shape in cutting plane A is shown with full lines, the cross-sectional shape in cutting plane B is shown with broken lines, and the cross-sectional shape in cutting plane C is shown with dot-and-dash lines. Finally, FIG. 6 shows the configuration of cutting plane D.

It will also be seen that the stem is grooved. The grooves 6 run parallel to the centre line of the stem and are separated by a rib 7 whose height (corresponding to the extent of the stem in the AP direction) remains constant between the cutting lines A and B and decreases only slightly towards the cutting line C. By contrast, the extent of the lateral and medial cross-sectional boundaries 8, 9 decreases comparatively more sharply. In the upper two thirds of the stem length, the groove base keeps approximately the same distance from the center plane 10 of the stem. From these features it follows that the groove flanks in the upper two thirds of the stem length provide a large surface area for the transmission of medially directed forces. In addition, particularly in the upper third, a large surface area is available for transmission in the vertical direction.

The stem surface is expediently designed for intimate connection with the natural bone tissue, for example roughened, or provided with a hydroxyapatite coating. This applies principally to the upper two thirds of the stem length, whilst the tip can, if appropriate, have a smooth design. As is known, the neck bearing is used for the additional transmission of forces to the resection surface. The grooves 6 can be continued through the area of the neck bearing in order to permit packing of bone material during implantation, or insertion of a releasing instrument in the case of implant removal.

The total curvature of the prosthesis stem corresponds approximately to the total directional change between the femoral neck 11 and the diaphysis 12. The almost uniform curvature permits insertion into a correspondingly preshaped bone cavity. The stem shape thus permits considerable freedom in the choice of the resection length L of the femoral neck, because the stem can be inserted to a greater or lesser extent before its lower end sets a limit by coming to bear against the hard cortical bone 13 of the diaphyseal or metaphyseal area.

In the operation, before insertion of the prosthesis stem, a rasp of the same shape can be used to prepare a cavity of the same shape. It is generally more expedient first to use a thinner tool to hollow out a narrower channel into which the prothesis stem is pressed, displacing the relatively soft, spongy bone material. By this means, in the case of cementless implantation, a more secure fit is achieved immediately after the operation. In addition, bone material can also be subsequently packed in by way of the grooves.

In the projection on the AP plane, the stem is expediently curved in accordance with the natural course of the bone. In the upper area, it exhibits the anteversion of the femoral neck.

FIG. 7 shows the determining of the stem contour of the prosthesis. The dot-and-dash lines show those circular arcs of which the contour is ideally composed. In FIG. 7, the lateral contour is designated La and the medial contour is designated M. Different sizes of prosthesis will of course be provided within a series. However, since the stems are essentially identical to each other, the ideal shape can be represented for all of them together and can be adapted by a conversion factor K which specifies the size ratio of the respective prosthesis in relation to the ideal shape and accordingly should in the present case be between 0.8 and 1.1.

The proximal section P is delimited on the medial side by a circular arc 20 whose radius expediently lies between 6 and 8 cm. In the illustrated example, it is 7.2 cm. The radius of the lateral arc 21 expediently lies between 11 and 14 cm, and, according to the example illustrated, is more preferably 12.4 cm. At the crossover point S, the proximal section ends and merges into the distal section D. At this point the arcs 20, 21 merge in the same direction into arcs with 22, 23. This means that the arcs 20 and 22 at the crossover point coincide in the shape of the arc 24, while the arcs 21 and 23 coincide in the shape of the arc 25. The arcs 24 and 25 deviate (corresponding to the wedge shape of the stem) at an angle α from one another. The angle of deviation is expediently 3 to 5° and, in the illustrated example, 3.8°.

The length of arc 22 on the lateral side of the distal section is expediently between 22 and 35 cm. In the illustrated example it is 27 cm. The radius 23 is expediently between 18 and 25 cm. In the illustrated example it is 21 cm. The distance between the lateral contour and the medial contour is most readily determined at the crossover point S. It is expediently between 1.7 and 2.1 cm, preferably between 1.8 and 2.0 cm. In the illustrated example it is 1.9 cm. In practice, small deviations from the ideal contour are to some extent unavoidable, and are to some extent desirable for adaptation to particular requirements. However, they should not be over 3 mm, preferably not over 2 mm. If, at some point, the true contour deviates from the ideal contour considerably in one direction, it should deviate from the ideal contour in the same direction on the opposite side. As has already been mentioned above, the given measurements are to be corrected according to the freely selectable factor K in accordance with the desired size of the prosthesis.

The prosthesis can be delivered with different stem sizes. The length of the prosthesis stem, measured in a straight line from the center of its attachment on the neck bearing to the tip, is expediently between 10 and 13 cm. Several sizes are expediently offered, for example with 105, 115 and 125 mm stem lengths. The arc of the upper two thirds of the stem length expediently extends over approximately 35 to 45 degrees, the curvature in the lower third over 2 to 10 degrees, preferably about 5 degrees. Although the neck emerges approximately in the same direction from the upper end of the stem, it may however enclose, with the latter, an acute angle of preferably 0 to 20 degrees. The sum of these angles forms the complementary angle to the so-called CCD angle, which is expediently between 110 and 130 degrees.

What is claimed is:

1. A hip-joint endoprosthesis, comprising:
   a curved stem that comprises a proximal portion and a distal portion and has a length of not more than 150 mm;
   a neck which adjoins an upper end of the stem and extends in a direction that is approximately the same as the direction of the upper end, and whose length is less than the length of an average femoral neck; and
   a joint head which is supported by the neck;
   wherein the stem is configured so as to deviate from a medial contour and a lateral contour by not more than 3 mm,
   the medial contour having a proximal section corresponding to the proximal portion of the stem that follows a circular arc with a radius of K×(6 cm to 8 cm) and a distal section corresponding to the distal portion of the stem that follows a contiguous circular arc co-directional with the circular arc of the proximal section of the medial contour and having a radius of K×(22 cm to 35 cm); and
   the lateral contour having a proximal section corresponding to the proximal portion of the stem that follows a circular arc with a radius of K×(11 cm to 14 cm), and a distal section corresponding to the distal portion of the stem that follows a contiguous circular arc co-directional with the circular arc of the proximal section of the lateral contour and having a radius of K×(18 cm to 25 cm); wherein the point where the proximal section of the medial contour meets the distal section of the medial contour is separated from the point where the proximal section of the lateral contour meets the distal section of the lateral contour by a distance of 1.7 to 2.1 cm,
   wherein a radius of the medial contour at the point where the proximal section of the medial contour meets the distal section of the medial contour forms an angle of 3° to 5° with respect to a radius of the lateral contour at the point where the proximal section of the lateral contour meets the distal section of the lateral contour; and
   wherein K is a constant in a range of between 0.8 and 1.1.

2. A hip-joint endoprosthesis according to claim 1, wherein the stem in a projection on an LM plane lies between two concentric circular arcs having a spacing equal to a thickness of the stem at the widest point of the stem.

3. A hip-joint endoprosthesis according to claim 2, wherein the two concentric circular arcs are also concentric to a center line of the stem in its upper half.

4. A hip-joint endoprosthesis according to claim 1, 2, or 3, wherein the stem has a plurality of deep grooves that run parallel to a center line of the stem.

5. A hip-joint endoprosthesis, comprising:
   a curved stem that comprises a proximal portion and a distal portion and has a length of not more than 150 mm;
   a neck which adjoins an upper end of the stem and extends in a direction that is approximately the same as the direction of the upper end, and whose length is less than the length of an average femoral neck; and
   a joint head which is supported by the neck;
   wherein the hip-joint endoprosthesis is available with different lengths of the neck; wherein the stem is configured so as to deviate from a medial contour and a lateral contour by not more than 3 mm,
   the medial contour having a proximal section corresponding to the proximal portion of the stem that follows a circular arc with a radius of K×(6 cm to 8 cm) and a distal section corresponding to the distal portion of the stem that follows a contiguous circular arc co-directional with the circular arc of the proximal section of the medial contour and having a radius of K×(22 cm to 35 cm); and
   the lateral contour having a proximal section corresponding to the proximal portion of the stem that follows a circular arc with a radius of K×(11 cm to 14 cm), and a distal section corresponding to the distal portion of the stem that follows a contiguous circular arc co-directional with the circular arc of the proximal section of the lateral contour and having a radius of K×(18 cm to 25 cm);
   wherein the point where the proximal section of the medial contour meets the distal section of the medial contour is separated from the point where the proximal section of the lateral contour meets the distal section of the lateral contour by a distance of 1.7 to 2.1 cm,
   wherein a radius of the medial contour at the point where the proximal section of the medial contour meets the distal section of the medial contour forms an angle of 3° to 5° with respect to a radius of the lateral contour at the point where the proximal section of the lateral contour meets the distal section of the lateral contour; and
   wherein K is a constant in a range of between 0.8 and 1.1.

6. A hip-joint endoprosthesis according to claim 5, wherein the stem in a projection on a plane including the medial contour and the lateral contour lies between two concentric circular arcs having a spacing equal to a thickness of the stem at the widest point of the stem.

7. A hip-joint endoprosthesis according to claim 6, wherein the two concentric circular arcs are also concentric to a center line of the stem in its upper half.

8. A hip-joint endoprosthesis according to claim 5, wherein the stem has a plurality of deep grooves that run parallel to a center line of the stem.

9. A hip-joint endoprosthesis according to claim 6, wherein the stem has a plurality of deep grooves that run parallel to a center line of the stem.

10. A hip-joint endoprosthesis according to claim 7, wherein the stem has a plurality of deep grooves that run parallel to a center line of the stem.

11. A hip-joint endoprosthesis according to claim 5, wherein the different neck lengths are obtained by a combination of the neck having a conical end and the joint head having a conical bore with said conical bore available in different sizes.

12. A hip-joint endoprosthesis according to claim 6, wherein the different neck lengths are obtained by a combination of the neck having a conical end and the joint head having a conical bore with said conical bore available in different sizes.

13. A hip-joint endoprosthesis according to claim 7, wherein the different neck lengths are obtained by a combination of the neck having a conical end and the joint head having a conical bore with said conical bore available in different sizes.

14. A hip-joint endoprosthesis according to claim 8, wherein the different neck lengths are obtained by a combination of the neck having a conical end and the joint head having a conical bore with said conical bore available in different sizes.

15. A hip-joint endoprosthesis according to claim 9, wherein the different neck lengths are obtained by a combination of the neck having a conical end and the joint head having a conical bore with said conical bore available in different sizes.

16. hip-joint endoprosthesis according to claim 10, wherein the different neck lengths are obtained by a combination of the neck having a conical end and the joint head having a conical bore with said conical bore available in different sizes.

* * * * *